United States Patent [19]
Paul et al.

[11] Patent Number: 5,814,088
[45] Date of Patent: Sep. 29, 1998

[54] CARDIAC STIMULATOR WITH LEAD FAILURE DETECTOR AND WARNING SYSTEM

[75] Inventors: Patrick J. Paul; David Prutchi, both of Lake Jackson, Tex.

[73] Assignee: Sulzer Intermedics Inc., Angleton, Tex.

[21] Appl. No.: 824,454

[22] Filed: Mar. 26, 1997

[51] Int. Cl.⁶ .................................................. A61N 1/37
[52] U.S. Cl. ............................................................ 607/28
[58] Field of Search .................. 607/8, 28, 9, 27

[56] References Cited

U.S. PATENT DOCUMENTS

| | | | |
|---|---|---|---|
| 4,964,407 | 10/1990 | Baker, Jr. et al. . | |
| 5,076,272 | 12/1991 | Ferek-Petric . | |
| 5,476,485 | 12/1995 | Weinberg et al. | 607/28 |
| 5,534,018 | 7/1996 | Wahlstrand et al. | 607/28 |
| 5,549,653 | 8/1996 | Stotts et al. | 607/4 |
| 5,609,614 | 3/1997 | Stotts et al. | 607/29 |
| 5,609,615 | 3/1997 | Sanders et al. | 607/36 |
| 5,643,328 | 7/1997 | Cooke et al. . | |

*Primary Examiner*—Scott M. Getzow
*Attorney, Agent, or Firm*—John R. Merkling; Fletcher, Yoder & Associates

[57] ABSTRACT

A method and apparatus for detecting failure or impending failure of a lead and for providing a warning to a patient or a patient's physician. The impedance of the lead is repeatedly measured and compared with certain impedance limits. If the measured impedance falls outside of these impedance limits, an alarm may be given to the patient, or a warning may be given to the patient's physician.

42 Claims, 8 Drawing Sheets

CARDIAC STIMULATOR WITH LEAD FAILURE DETECTOR AND WARNING SYSTEM

BACKGROUND OF THE INVENTION

1. Field of the Invention

This present invention relates generally to cardiac stimulators and, more particularly, to a failure detector and warning system for a cardiac stimulator.

2. Description of the Related Art

As most people are aware, the human heart is an organ having four chambers. A septum divides the heart in half, with each half having two chambers. The upper chambers are referred to as the left and right atria, and the lower chambers are referred to as the left and right ventricles. Deoxygenated blood enters through the right atrium through the vena cava. Contraction of the right atrium and of the right ventricle pump the deoxygenated blood through the pulmonary arteries to the lungs where the blood is oxygenated. This oxygenated blood is carried to the left atrium by the pulmonary veins. From this cavity, the oxygenated blood passes to the left ventricle, which pumps the blood to a large artery called the aorta. The aorta delivers the pure blood to the other portions of the body through the various branches of the vascular system.

For a variety of reasons, a person's heart may not function properly and, thus, endanger the person's well-being. Medical devices have been developed to facilitate heart function. For instance, if a person's heart does not beat properly, a cardiac stimulator may be used to provide relief. A cardiac stimulator is a medical device that delivers electrical stimulation to a patient's heart. Cardiac stimulators generally fall into two categories, pacemakers and defibrillators, although some cardiac stimulators may perform both functions. Pacemakers supply electrical pulses to the heart to keep the heart beating at a desired rate. Defibrillators supply a relatively larger electrical pulse to the heart to help the heart recover from cardiac fibrillation.

Regardless of type, implantable cardiac stimulators are battery powered devices that are typically implanted into a patient's chest wall. Implantable cardiac stimulators include a hermedically sealed case that contains the battery as well as the electrical circuitry used to provide the functions of the cardiac stimulator. This electrical circuitry generally includes a pulse generator for creating electrical stimulation pulses. A cardiac stimulator also generally includes at least one lead. The proximal end of the lead is coupled to the cardiac stimulator. The distal end of the lead is usually inserted into one of the patient's body vessels and guided into the heart. The distal end of the lead typically includes an electrode that attaches to the inner wall of the heart to establish the required electrical connection between the cardiac stimulator and the heart. Not only does the lead transmit the electrical stimulation pulses to the heart, the lead may also transmit electrical signals sensed from the heart to the electrical circuitry contained within the case.

As can be appreciated, as cardiac stimulators have become more complex, the electronic circuitry used to implement the cardiac stimulator's functions has also become more complex. In fact, most cardiac stimulators currently employ a microprocessor that controls much of the complex functionality of the pacemaker. Given the complexity of a current cardiac stimulator's circuitry and the number of parameters sensed and adjusted by the cardiac stimulator, it is not surprising that certain circumstances may exist that cause the cardiac stimulator to malfunction. As cardiac stimulators have evolved, however, painstaking efforts have been made not only to avoid system failures, but also to prevent system failures from adversely affecting the patient. For instance, many cardiac stimulators are capable of monitoring themselves and generating a fault signal if a possible malfunction is detected. If a fault condition exists, a cardiac stimulator operating in a complex mode may revert to a less complex mode, typically referred to as a backup mode. In the backup mode the cardiac stimulator may operate in a less efficient and less complex fashion, but it still maintains the basic functionality for maintaining patient safety.

In addition to overriding a system failure, cardiac stimulators may present a warning to a patient if a failure or an impending failure is detected. These warning systems may use a variety of different alarms to warn a patient in response to the detection of a failure or an impending failure. As one example, a tone generator may be placed within the cardiac stimulator. The tone generator emits an intermittent sound in response to an alarm condition. Disadvantageously, however, because the tone generator is contained within the cardiac stimulator, which is implanted under layers of tissue, the sound is considerably attenuated. Hence, it is difficult for patients to perceive this warning. As another example, a vibrator may be coupled to a cardiac stimulator to emit a vibration in response to the detection of an alarm condition. Unfortunately, vibrators are quite large and tend to consume much energy. By way of yet another example, a cardiac stimulator may include an electrode that is coupled to a skeletal muscle. The cardiac stimulator delivers a charge to the electrode in response to an alarm condition to cause the skeletal muscle to twitch.

A variety of detected failures or impending failures may trigger a warning. As one example, the batteries that power cardiac stimulators have a finite life. Although great strides have been made in the design of long life batteries and power stingy cardiac stimulators, a cardiac stimulator's batteries will eventually deteriorate. As the batteries become depleted, the operation of the cardiac stimulator may begin to suffer. For instance, low battery power may cause the electrical circuitry to operate improperly, or sufficient power may not be available to stimulate the myocardial tissue adequately. Thus, if a cardiac stimulator detects a low battery condition, it may emit a warning to prompt the patient to visit a physician before the condition adversely affects the patient.

Of course, batteries are not the only constituent of a cardiac stimulator that might fail. For instance, it can be readily appreciated that a lead's operating environment can be quite harsh. In addition to traversing winding body vessels, a lead is also subjected to virtually constant movement due to the beating of the heart. Accordingly, to facilitate placement of the lead within the heart, as well as the longevity of the lead during subsequent use, leads are made to be quite flexible. Typically, a lead includes an outer tubing that is composed of a flexible biocompatible material. One or more flexible conductors are disposed within this flexible outer tubing for transmitting electrical signals between the cardiac stimulator and the electrode.

In spite of tremendous advances in lead technology, leads tend to fail from time to time. If a lead were to fail catastrophically, such as if the lead were to break in half or if the electrode were to become dislodged, then communication between the cardiac stimulator and the body tissue could be lost. In other words, the lead could not send sensing signals to the cardiac stimulator, and the cardiac stimulator could not deliver electrical stimulation pulses to the heart.

Fortunately, however, leads tend to fail gradually. For instance, leads quite commonly carry multiple conductors. It is quite unusual for all of these conductors to break at the same time. Rather, these conductors tend to break one at a time. The breaking of one conductor may have little or no affect on the operation of the cardiac stimulator. However, as more conductors break, the functionality of the cardiac stimulator may deteriorate rapidly. Therefore, it would be useful if lead failure could be detected at an early stage so that the lead could be replaced before the patient is adversely affected by the deteriorating lead.

Although the warning systems have been used to notify patients of various alarm conditions, they have not been used to warn patients of the failure or impending failure of a lead. The primary reason for this omission is that lead failure is so difficult to detect. At first blush, it might seem reasonable merely to measure the impedance of a lead to determine whether it has failed. However, it is difficult to determine a lead's condition in this manner, because so many factors may influence changes in the lead's impedance. Factors that may cause changes in the impedance of a lead include scar tissue formed around the electrode at the end of the lead, lead movement, and physiological changes. Another factor discouraging automated monitoring of the condition of a lead relates to the wide variety of leads available for use with a particular cardiac stimulator. Because the impedance of different leads vary, and because impedance changes for different leads and different implants vary, the problem of automated monitoring is further exacerbated.

As a result of these problems, the patient's attending physician typically measures lead impedance during routine checkups and interprets any change in impedance based on the physician's experience. Thus, the patient must trust that the physician is experienced enough to determine whether a lead has broken or become dislodged.

The present invention may address one or more of the problems set forth above.

SUMMARY OF THE INVENTION

In accordance with one aspect of the present invention, there is provided a cardiac stimulator. The cardiac stimulator includes means for measuring impedance of a lead; means for comparing the measured impedance with an upper impedance limit and a lower impedance limit; and means for activating an alarm in response to the measured impedance being one of greater than the upper impedance limit and less than the lower impedance limit.

In accordance with another aspect of the present invention, there is provided a cardiac stimulator. The cardiac stimulator includes means for receiving data correlative to repeated impedance measurements of a lead. The cardiac stimulator further includes means for calculating a maximum impedance limit and a minimum impedance limit in response to a first of the repeated impedance measurements. There is also provided means for calculating an upper impedance limit and a lower impedance limit in response to each of the repeated impedance measurements. The cardiac stimulator also includes means for determining whether the data correlative to each of the repeated impedance measurements is greater than one of the maximum impedance limit and the upper impedance limit and is less than one of the minimum impedance limit and the lower impedance limit. There is also provided means for generating an alarm initiation signal in response to the data correlative to one of the repeated impedance measurements being greater than one of the maximum impedance limit and the upper impedance limit or being less than one of the minimum impedance limit and the lower impedance limit.

In accordance with a still another aspect of the present invention, there is provided a cardiac stimulator that includes a lead adapted to transmit electrical signals to a heart. The cardiac stimulator also includes means for measuring impedance of the lead. There is also provided means for determining whether the measured impedance is within a given impedance range and for delivering an alarm signal in response to the measured impedance being outside the given range. The cardiac stimulator also includes means for delivering an alarm in response to the alarm initiation signal.

In accordance with yet another aspect of the present invention, there is provided a cardiac stimulator that includes a lead adapted to transmit electrical signals. The cardiac stimulator also includes an impedance measurement circuit for measuring impedance of the lead. There is provided a comparison circuit for comparing the measured impedance with an impedance limit. The comparison circuit delivers an alarm initiation signal in response to the measured impedance differing from the impedance limit by a given magnitude. There is also provided an alarm circuit for activating an alarm in response to the alarm initiation signal.

In accordance with a further aspect of the present invention, there is provided a cardiac stimulator that includes a lead adapted to transmit electrical signals to a heart. An impedance measurement circuit is coupled to the lead. A control circuit is coupled to the impedance measurement circuit. The impedance measurement circuit measures impedance of the lead in response to receiving a first control signal from the control circuit. A comparison circuit determines whether the measured impedance is within a given impedance range. The comparison circuit delivers an alarm initiation signal in response to the measured impedance being outside the given range. An alarm circuit delivers an alarm in response to the alarm initiation signal.

In accordance with a still further aspect of the present invention, there is provided a software program for use with a cardiac stimulator. The program includes a routine for receiving data correlative to an impedance measurement of a lead. The program also includes a routine for determining whether the impedance measurement data is within a given impedance range. The program further includes a routine for generating an alarm initiation signal in response to the measured impedance being outside the given range.

In accordance with a yet further aspect of the present invention, there is provided a software program for use with a cardiac stimulator. The program includes a routine for receiving data correlative to repeated impedance measurements of a lead. The program also includes a routine for calculating a maximum impedance limit and a minimum impedance limit in response to a first of the repeated impedance measurements. The program further includes a routine for calculating an upper impedance limit and a lower impedance limit in response to each of the repeated impedance measurements. There is provided a routine for determining whether the data correlative to each of the repeated impedance measurements is greater than one of the maximum impedance limit and the upper impedance limit and is less than one of the minimum impedance limit and the lower impedance limit. There is also provided a routine for generating an alarm initiation signal in response to the data correlative to one of the repeated impedance measurements being greater than one of the maximum impedance limit and the upper impedance limit or being less than one of the minimum impedance limit and the lower impedance limit.

In accordance with another aspect of the present invention, there is provided a method of detecting failure of a lead used with a cardiac stimulator. The method includes the steps of: (a) measuring impedance of the lead; (b) comparing the impedance of the lead with an impedance limit; and (c) activating an alarm in response to the impedance of the lead differing from the impedance limit in a given manner.

In accordance with still another aspect of the present invention, there is provided a method of detecting failure of a lead used with a cardiac stimulator. The method includes the steps of: (a) measuring impedance of the lead; (b) determining whether the impedance of the lead is within a given impedance range; and (c) generating an alarm initiation signal in response to the impedance of the lead being outside the given impedance range.

In accordance with yet anther aspect of the present invention, there is provided a method of detecting failure of a lead used with a cardiac stimulator. The method includes the steps of: (a) repeatedly measuring impedance of the lead; (b) calculating a maximum impedance limit and a minimum impedance limit in response to a first of the repeated impedance measurements; (c) calculating an upper impedance limit and a lower impedance limit in response to each of the repeated impedance measurements; (d) determining whether each of the repeated impedance measurements is greater than one of the maximum impedance limit and the upper impedance limit and is less than one of the minimum impedance limit and the lower impedance limit; and (e) generating an alarm initiation signal in response to one of the repeated impedance measurements being greater than the maximum impedance limit and the upper impedance limit or being less than one of the minimum impedance limit and the lower impedance limit.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
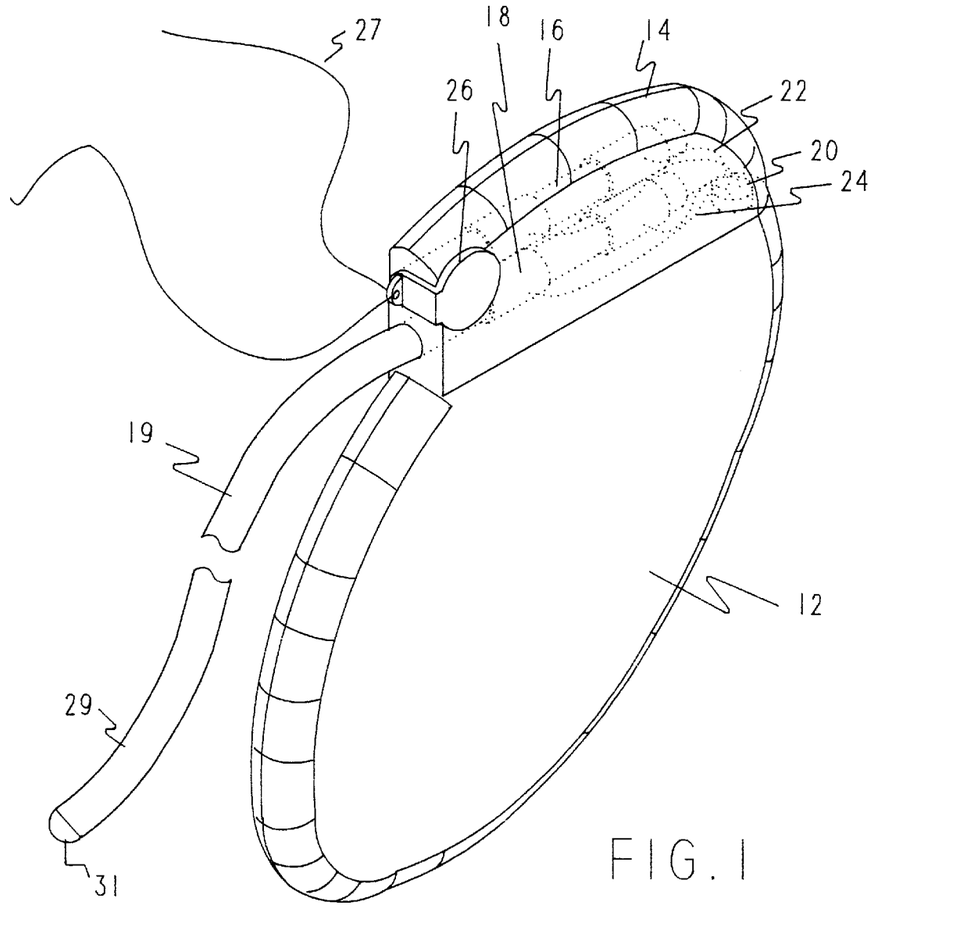
FIG. 1 illustrates a perspective view of a dual chamber cardiac stimulator having a pin electrode and a lead.

Turning now to the drawings, and referring initially to FIG. 1, a cardiac stimulator is illustrated and generally designated by a reference numeral 10. For the purposes of this discussion, the cardiac stimulator 10 is illustrated as a dual chamber pacemaker. However, it is currently believed that other cardiac stimulators, such as single chamber pacemakers, cardioverters, and defibrillators, may also be used in accordance with the teachings provided herein.

The cardiac stimulator 10 includes a hermetically sealed case 12. The case 12 contains electrical circuitry used for performing various functions of the cardiac stimulator 10, as well as batteries for powering the electrical circuitry and for providing the energy used for delivering electrical stimulation pulses to the patient. A header 14 is attached to the case 12. Because a dual chamber pacemaker is illustrated in this embodiment, the header 14 includes two sockets 16 and 18. A lead, such as the lead 19, may be electrically and mechanically connected to the cardiac stimulator 10 via one of the sockets 16 and 18. The lead 19 places the cardiac stimulator 10 in electrical communication with the heart or other body tissues. Electrical conductors 22 and 24 pass through a feed-through 20 to provide an electrical connection between the sockets 16 and 18, respectively, and the electrical circuitry within the case 12.

A dual chamber pacemaker typically utilizes two leads, one connected to each socket 16 and 18, for stimulating the heart. For example, a lead connected to the socket 18 would usually be used to sense and stimulate the ventricle of the heart, while a lead connected to the socket 16 would usually be used to sense and stimulate the atrium of the heart. However, as will be explained in greater detail below, the socket 16 of the cardiac stimulator 10 is coupled to a pin electrode 26 rather than a lead. The pin electrode 26 is coupled to excitable tissue of a patient, typically by the use of a suture 27. The excitable tissue may be a skeletal muscle, a nerve ending, or other tissue capable of a perceptible physiological reaction in response to electrical stimulation. When the cardiac stimulator 10 detects an alarm condition, as described below, it delivers an electrical stimulation pulse via the socket 16 to the pin electrode 26. Because the pin electrode 26 is coupled to one of the patient's muscles, for instance, this electrical stimulation pulse causes the muscle to twitch. The twitching muscle warns the patient that the cardiac stimulator 10 has detected an alarm condition, so that the patient may visit a physician for further evaluation.

Because the pin electrode 26 is coupled to the socket 16, only one lead 19 may be coupled to the cardiac stimulator 10 via the socket 18. Accordingly, the dual chamber pacemaker in this embodiment is programmed to operate as a single chamber pacemaker. Advantageously, because of the larger batteries usually provided in dual chamber pacemakers, a dual chamber pacemaker used in single chamber mode can be expected to last a significantly longer period of time as compared to a similar single chamber pacemaker.

As mentioned previously, the case 12 contains the cardiac stimulator's electrical circuitry. Although it is possible that this electrical circuitry may take various forms, one embodiment is illustrated by the block diagram of FIG. 2. To the extent that the actual circuitry of a particular block is deemed useful in describing the manner in which the cardiac stimulator 10 detects a possible lead failure and provides a warning, the actual circuitry will be illustrated and discussed. However, as mentioned previously, much of the electrical circuitry exists in ordinary dual chamber pacemakers, such as Intermedics model no. 294-03, and, thus, need not be described in detail herein.

Figure 2:
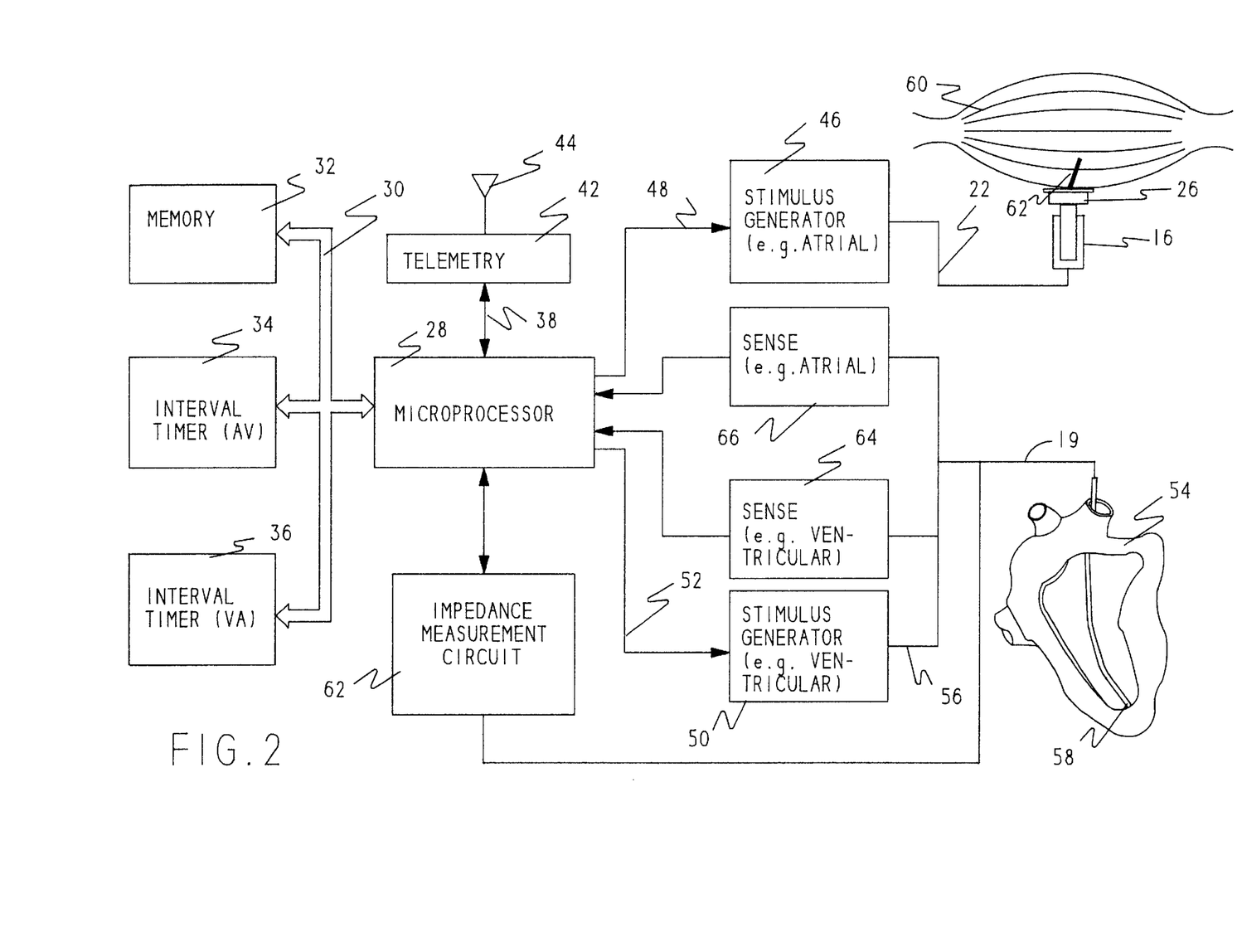
FIG. 2 illustrates a block diagram of a cardiac stimulation system.

As can be seen, the electrical circuitry includes a microprocessor 28 that provides control and computational facilities for the cardiac stimulator 10. The microprocessor 28 is coupled to a variety of other circuits via a bi-directional bus 30. In this embodiment, for instance, the bus 30 couples the microprocessor 28 to a memory 32 and interval timers 34 and 36. A bi-directional bus 38 also couples the microprocessor 28 to a telemetry circuit 42.

The memory 32 advantageously includes both random access memory (RAM) and read only memory (ROM). Generally speaking, the ROM stores programs and other parameters used by the microprocessor 28, such as parameters programmed into the cardiac stimulator 10 by a physician. The RAM stores parameters and portions of programs currently being used by the microprocessor 28 during operation of the cardiac stimulator 10. The microprocessor 28 may also include internal memory used for storing various programs or parameters.

The interval timers 34 and 36 may be external to the microprocessor 28, as illustrated, or internal to the microprocessor 28. The timers 34 and 36 may be conventional up or down counters of a type initially loaded with a count value. The interval timers 34 and 36 typically count up to or down from the count value and output a roll-over bit upon completing the programmed count. If the cardiac stimulator 10 is used as a dual chamber pacemaker, the interval timers 34 and 36 may be used to time AV and VA intervals. Alternatively, if the cardiac stimulator 10 is programmed to function as a single chamber pacemaker, one of the interval timers 34 or 36 may be used to time an A/A or V/V interval, depending upon whether the atrium or ventricle of the heart is being sensed and paced.

The telemetry circuit 42 facilitates communication between the cardiac stimulator 10 and a programming device (not shown) located external to the patient's body. The telemetry circuit 42 communicates with the programming device via an antenna 44. Using the programming device, a physician may program various parameters into the memory 32 to tailor the cardiac stimulator's functionality to a patient's particular situation.

Because the cardiac stimulator 10 is illustrated as a typical dual chamber pacemaker in this embodiment, the microprocessor 28 is coupled to stimulus and sensing circuits for the atrium and the ventricle. As illustrated, line 48 couples the microprocessor 28 to an atrial stimulus generator 46 that is ordinarily used to produce pulses for stimulating the atrium. The control line 52 couples the microprocessor 28 to a ventricular stimulus generator 50 that is ordinarily used to produce stimulation pulses for stimulating the ventricle. However, as mentioned previously, the dual chamber pacemaker is programmed to operate in a single chamber mode because the pin electrode 26 is coupled to the socket 16 for stimulating a muscle. Therefore, as illustrated in FIG. 2, the atrial stimulus generator 46 is coupled to the pin electrode 26 via the conductor 22 and the socket 16. The pin electrode 26 is coupled to a muscle 60 by the suture 27. The suture 27 may also be electrically conductive to provide additional stimulus to the muscle 60.

The ventricular stimulus generator 50, on the other hand, which would ordinarily be used to stimulate the ventricle, is coupled to the lead 19 by a control line 56. The electrode 31 at the distal end 29 of the lead 19 is disposed within the heart 54 to stimulate either the atrium or the ventricle. In this embodiment, the electrode 31 of the lead 19 is illustrated as being disposed in the ventricle 58 of the heart 54.

The electrical condition of the heart 54 may be sensed and delivered to the microprocessor 28. An ordinary dual chamber pacemaker includes a ventricular sense circuit 64 and an atrial sense circuit 66. The ventricular sense circuit 64 and the atrial sense circuit 66 ordinarily receive signals from the leads and transmit these signals to the microprocessor 28. Because the lead 19 in this embodiment delivers electrical stimulation to the ventricle 58, the ventricular sense circuit 64 is used in a normal manner to detect the occurrence of R waves and to transmit this information to the microprocessor 28. The atrial sense circuit 66 may not be used in this embodiment because neither stimulus generator 46 or 50 is coupled to the atrium of the heart 54.

Based, in part, on the information delivered to it by the atrial sense circuit 66 and the ventricular sense circuit 64, the microprocessor 28 controls the timing of the ventricular stimulus generator 50. Of course, the microprocessor 28 may base its control of the ventricular stimulus generator 50 on other parameters, such as information received from other sensors (not shown). For example, an activity sensor (not shown), such as an implanted accelerometer, may be used to gather information relating to changing levels of patient activity.

When operating in a dual chamber mode, the microprocessor 28 would normally be programmed to control the atrial stimulus generator 46 and the ventricular stimulus generator 50 to provide periodic pulses to the atrium and ventricle of the heart. However, as discussed above, the atrial stimulus generator 46 is coupled to the pin electrode 26 rather than a lead. Hence, the microprocessor 28 is programmed so that it controls the atrial stimulus generator 46 to deliver an electrical stimulation signal to the pin electode 26 when the microprocessor 28 determines that an alarm condition exists.

To determine the existence of an alarm condition, the impedance of the lead 19 is measured by an impedance measurement circuit 62, which is coupled between the lead 19 and the microprocessor 28. Although different methods and apparatus might be suitable for measuring the impedance of the lead 19, this particular embodiment uses the pacing circuitry illustrated in FIG. 3. The pacing and impedance measurement circuit 62 is coupled to the lead 19 by a d.c. blocking capacitor 64, which may have a value of 10 microfarads, for example. The blocking capacitor 64 is commonly used to prevent d.c. current from reaching the lead 19 and causing unwanted ionic imbalance, electrolysis, and other deleterious effects. An active discharge switch 66 is coupled between the capacitor 64 and circuit ground. A passive discharge resistor 68, which advantageously has a high impedance, e.g., 100k ohms, as compared with the lead impedance, is also coupled between the capacitor 64 and circuit ground. The active discharge switch 66 is closed for a short period, e.g., about 20 milliseconds, after pacing, so that it works in conjunction with the passive discharge resistor 68 to discharge the blocking capacitor 64.

Figure 3:
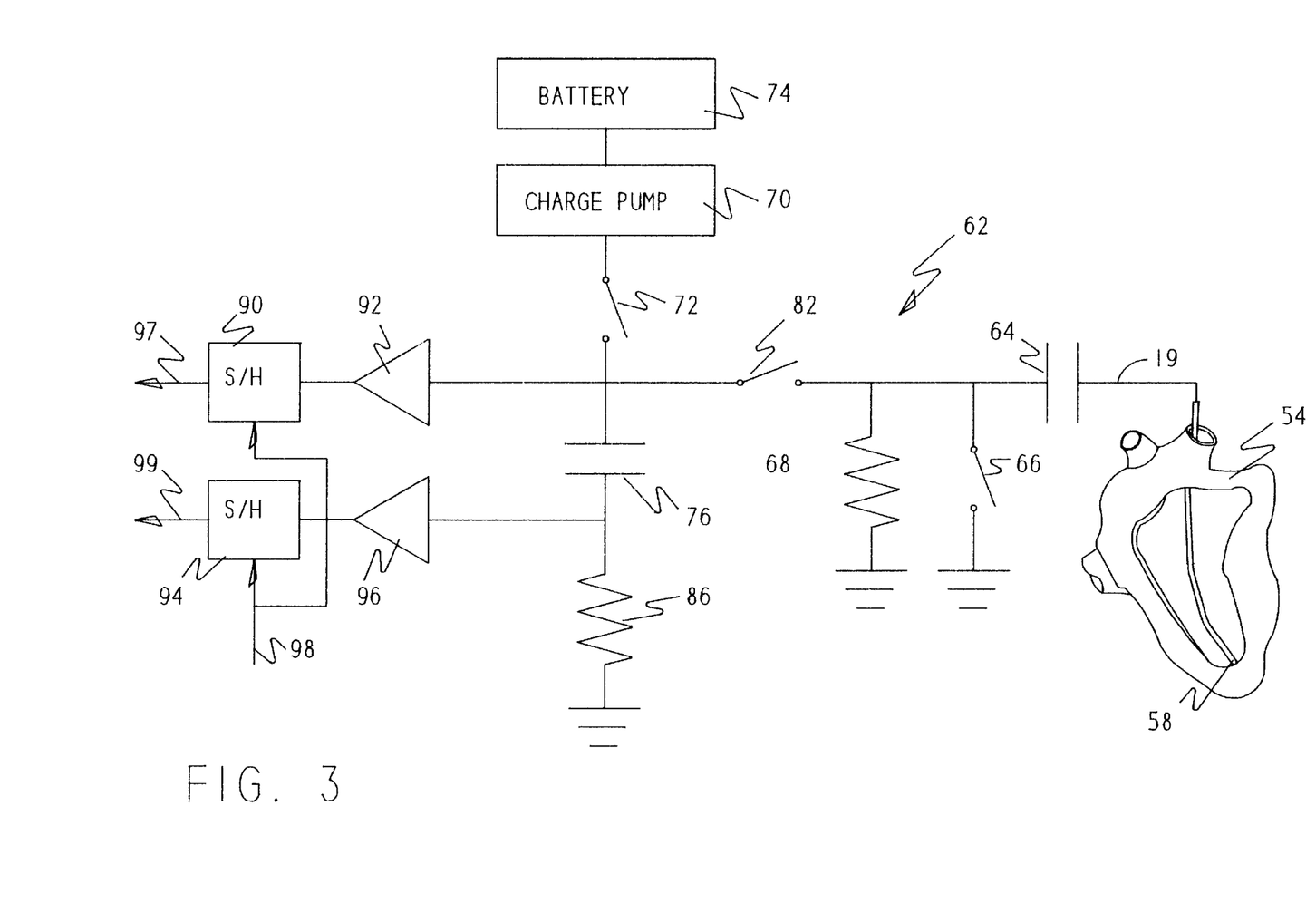
FIG. 3 illustrates a schematic diagram of an impedance measurement circuit used with the cardiac stimulation system of FIG. 2.

To provide an electrical charge sufficient to stimulate the heart, a charge pump 70 having a charge switch 72 is coupled to the battery 74 of the cardiac stimulator 10. The charge pump 70 charges a tank capacitor 76, which may have a value of about 10 microfarads, when the charge switch 72 is closed. This may be seen by referring to FIGS.

Figure 4A:
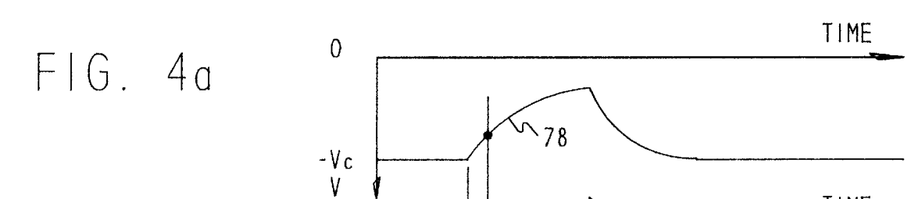
FIG. 4a illustrates a curve of tank capacitor voltage as a function of time.
Figures 4B, 4C:
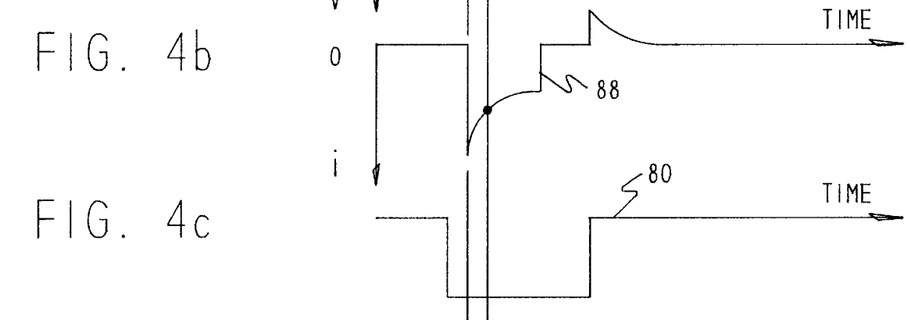
FIG. 4b illustrates a curve of measurement resistor current as a function of time.
FIG. 4c illustrates states of a charge switch as a function of time.

4a and 4c. In this embodiment, the cardiac stimulator 10 delivers a negative voltage to the heart. Thus, the curve 78 of FIG. 4a illustrates that the charge on the tank capacitor 76 is $-V_c$ when the charge switch 72 is in its closed state as illustrated by the curve 80 in FIG. 4c. Because the charge pump 70 is capable of producing a voltage having a magnitude greater than the battery voltage, the magnitude of the charge voltage $-V_c$ may be larger than the magnitude of the battery voltage.

Figure 4D:
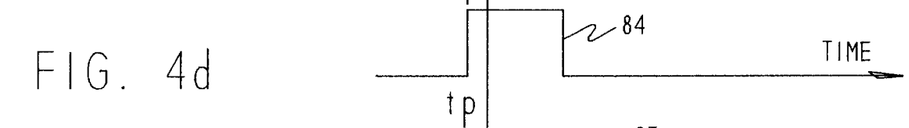
FIG. 4d illustrates states of a pacing switch as a function of time.

To deliver this electrical charge to the lead 19, the microprocessor 28 switches a pacing switch 82 from its open state to its closed state at time $t_p$, as illustrated by the curve 84 of FIG. 4d. It should be noticed that the microprocessor 28 switches the charge switch 72 from its closed state to its open state just before it closes the pacing switch 82. Also, as mentioned previously, the active discharge switch 66 is open when the pacing switch 82 is closed.

To measure the resistance of the lead, a current measurement resistor 86 is coupled in series between the tank capacitor 76 and circuit ground. The value of the current measurement resistor 86 is advantageously much less than the impedance of the lead 19. Because lead impedance is typically between about 150 ohms and 2000 ohms, the value of the current measurement resistor 86 may be in the range of 10 to 20 ohms, for instance. As illustrated by the curve 88 of FIG. 4b, no current passes through the measurement resistor 86 until the tank capacitor 76 begins to discharge at time $t_p$. Current continues to flow through the measurement resistor 86 until the pacing switch 82 is opened. A small current may also flow through the measurement resistor 86 when the charge switch 72 is closed at time $t_c$ to recharge the tank capacitor 76.

Figure 4E:
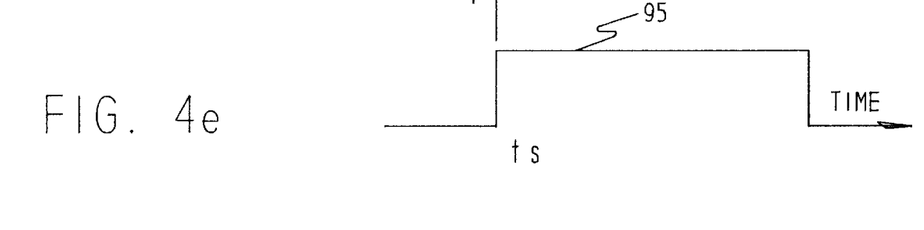
FIG. 4e illustrates states of a sample signal as a function of time.

Because closure of the pacing switch 82 couples the tank capacitor 76 and the measurement resistor 86 to the lead 19, the voltage across the tank capacitor 76 and/or the current flowing through the measurement resistor 86 may be measured when the pacing switch 82 is closed in order to measure the resistance of the lead 19. To measure the voltage across the tank capacitor 76, a sample and hold circuit 90 is coupled via an amplifier 92 between one terminal of the tank capacitor 76 and the pacing switch 82. To measure the current flowing through the measurement resistor 86, another sample and hold circuit 94 is coupled via an amplifier 96 between the other terminal of the tank capacitor 76 and the measurement resistor 86. The sample and hold circuits 90 and 94 are coupled together by a control line 98. When the microprocessor 28 delivers a sample signal, illustrated by the curve 95 in FIG. 4e, the sample and hold circuits 90 and 94 make their respective voltage and current measurements. In this embodiment, this measurement is made at time $t_s$, which is about 10 microseconds after closure of the pacing switch 82 at time $t_p$.

The sample and hold circuits 90 and 94 deliver the respective voltage and current signals to the microprocessor 28 via lines 97 and 99, respectively. The microprocessor 28 may determine the impedance of the lead 19 using Ohm's law. In other words, the voltage value from the line 97 is divided by the current value from the line 99 to render a resistance value. However, this resistance value includes not only the lead resistance, but also the resistance of other portions of the measurement circuit. In this embodiment, for instance, this resistance value includes the resistance of the pacing switch 82. Therefore, these known resistance value is subtracted from the measured resistance to yield the resistance of the lead 19.

As stated earlier, the resistance of the lead 19 may change over time. One example of how the impedance of a lead may vary over time is depicted by the curve 100 illustrated in FIG. 5. The curve 100 depicts the measured impedance of the lead 19 from the time of implant $t_0$. As can be seen, the impedance of the lead 19 can vary substantially depending upon a number of circumstances. These variations may occur as a result of tissue encapsulating the electrode of the lead, the dislodgment of the lead's electrode, breakage of the lead, or other physiological changes. Typically, relatively slow variation of the lead's impedance are normal. However, relatively fast changes in impedance are not normal and, thus, may indicate possible lead failure.

To provide an automatic method of determining a possible lead failure, the microprocessor 28 contains a program that calculates certain limits based primarily on the initial impedance of the lead 19 and subsequent variations in impedance of the lead 19. The main steps of this program are depicted by the flow chart 110 illustrated in FIG. 6. First, the physician implants the lead 19 into the patient's heart 54 at time $t_0$. See block 112. The microprocessor 28 controls the impedance measurement circuit 62 to measure the initial impedance of the lead 19. See block 114. This initial impedance is illustrated as the point $Z_i$ in FIG. 5. The physician may initiate the initial impedance measurement during the implantation procedure as part of the physician's normal programming routine, or the microprocessor 28 may initiate the initial impedance measurement at the time of start up or in response to a subsequent timing signal.

Figure 5:
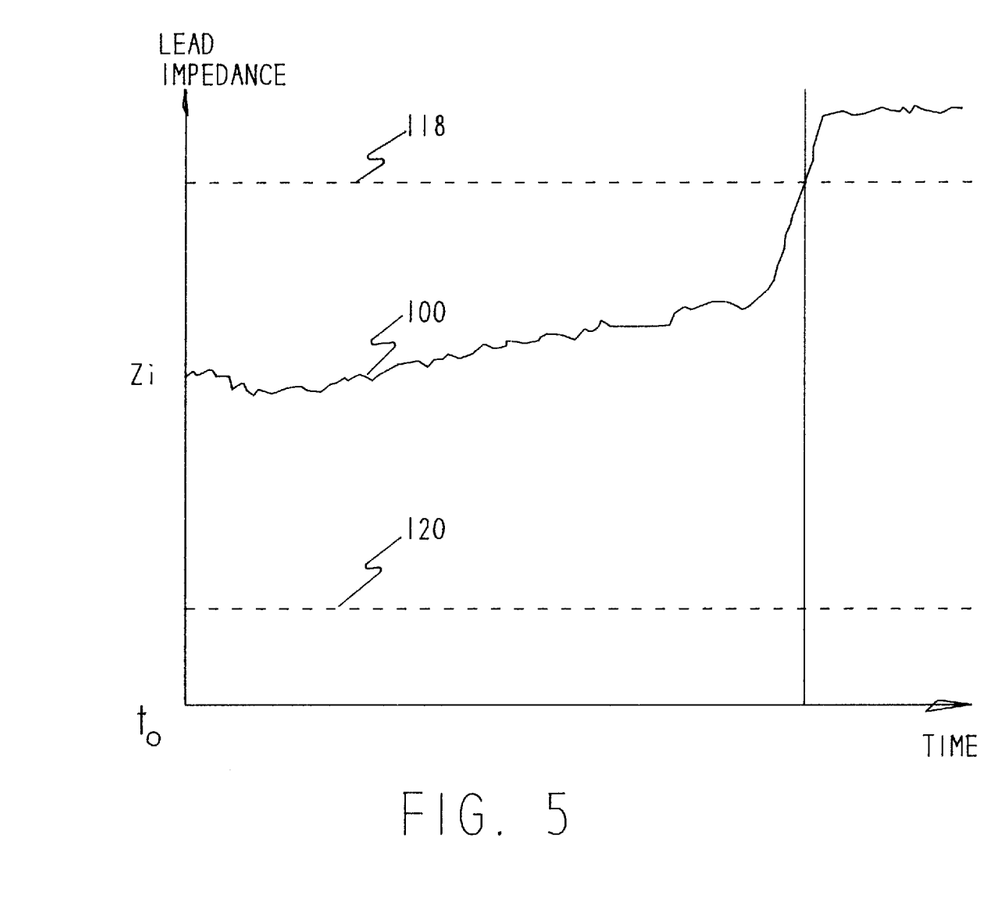
FIG. 5 illustrates a graph of measured lead impedance as a function of time, along with maximum and minimum absolute limits of impedance.

Once the lead's starting impedance $Z_i$ has been measured, the microprocessor 28 computes upper and lower absolute limits based on this initial impedance value $Z_i$. These absolute impedance limits are illustrated in FIG. 5 by a dashed line 118, which illustrates the maximum allowable impedance, and by a dashed line 120, which illustrates the minimum allowable impedance. The maximum and minimum absolute limits 118 and 120 may be calculated by multiplying the initial impedance $Z_i$ by respective coefficients—one to calculate the maximum absolute limit 118 and the other to calculate the minimum absolute limit 120. Alternatively, the maximum absolute limit 118 and the minimum absolute limit 120 may be preselected depending upon the type of lead 19 that is used. For instance, if a ThinLine lead, available from the present assignee, is used, the maximum absolute limit 118 may be set at 800 ohms, because it is unlikely that the impedance of a ThinLine lead would reach 800 ohms under normal operating conditions and, thus, an 800 ohm reading would probably indicate that the lead has broken. Similarly, the minimum limit 120 for a ThinLine lead may be set at 150 ohms, because it is unlikely that the impedance of a ThinLine lead would ever drop below 150 ohms in normal operating conditions. These coefficients and/or absolute limit values may be preset or programmable by the physician. Of course, the absolute limits 118 and 120 need not be set to reflect a worse case scenario. Rather, the absolute limits 118 and 120 could be set to reflect various levels of deterioration of a lead.

Figure 6:
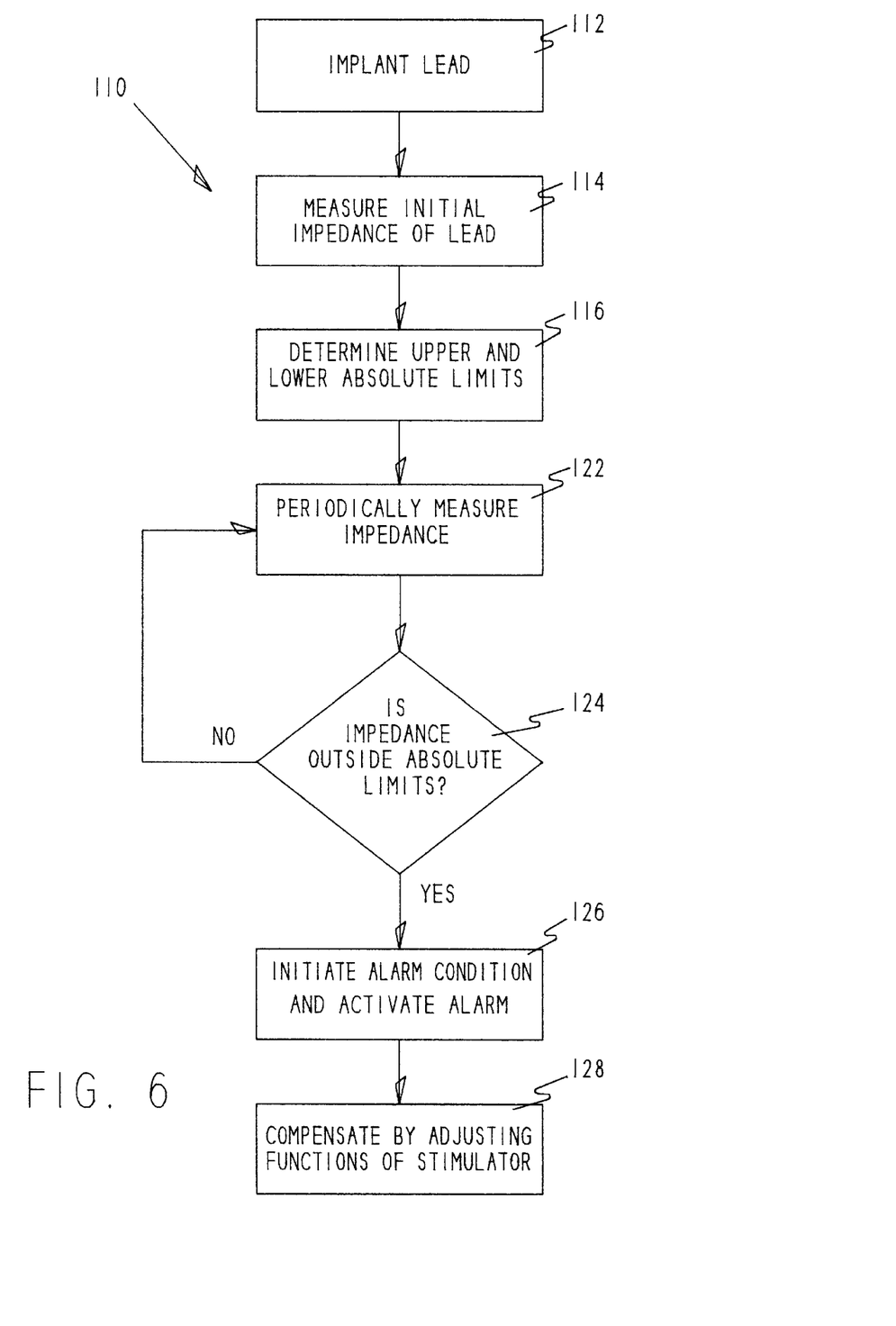
FIG. 6 illustrates a flowchart depicting a failure detection operating mode of the cardiac stimulation system of FIG. 2.

Once the absolute maximum limit 118 and the absolute minimum limit 120 have been set, the impedance of the lead 19 is periodically measured. See block 122. The impedance may be measured once a day, once per week, once per month, or in response to certain circumstances, such as after every 10,000$^{th}$ heart beat or after every period of increased heart rate. This measured impedance is compared to the maximum absolute limit 118 and the minimum absolute limit 120 to determine if it is outside of the selected range. See block 124. If not, the microprocessor 28 takes no action other than to measure the impedance at a later time. See block 122.

However, if the impedance of the lead 19 crosses one of the absolute limits 118 or 120, such as at time $t_a$, an alarm condition is initiated. See block 126. In response to this alarm condition, the microprocessor 28 delivers a signal on line 48 to the stimulus generator 46. The stimulus generator 46 delivers an electrical stimulation pulse to the pin electrode 26. The magnitude and duration of this pulse is sufficient to inform the patient of the existence of an alarm condition. The pulse is delivered periodically until the patient visits a physician who deactivates the warning signal and determines the cause of the alarm condition.

In addition to warning the patient, certain functions of the cardiac stimulator 10 may also be adjusted to compensate for the cause of the alarm condition. See block 128. For instance, the cardiac stimulator 10 may automatically increase the output amplitude and pulse duration delivered by the ventricular stimulus generator 50 to maximize the possibility of capture in the event that the impedance change is indeed related to a failure which would elevate the threshold for capture. Types of lead failure which could elevate the capture threshold include dislocation of the electrode, micro dislocations, partial lead fracture, or shunting.

Figure 7:
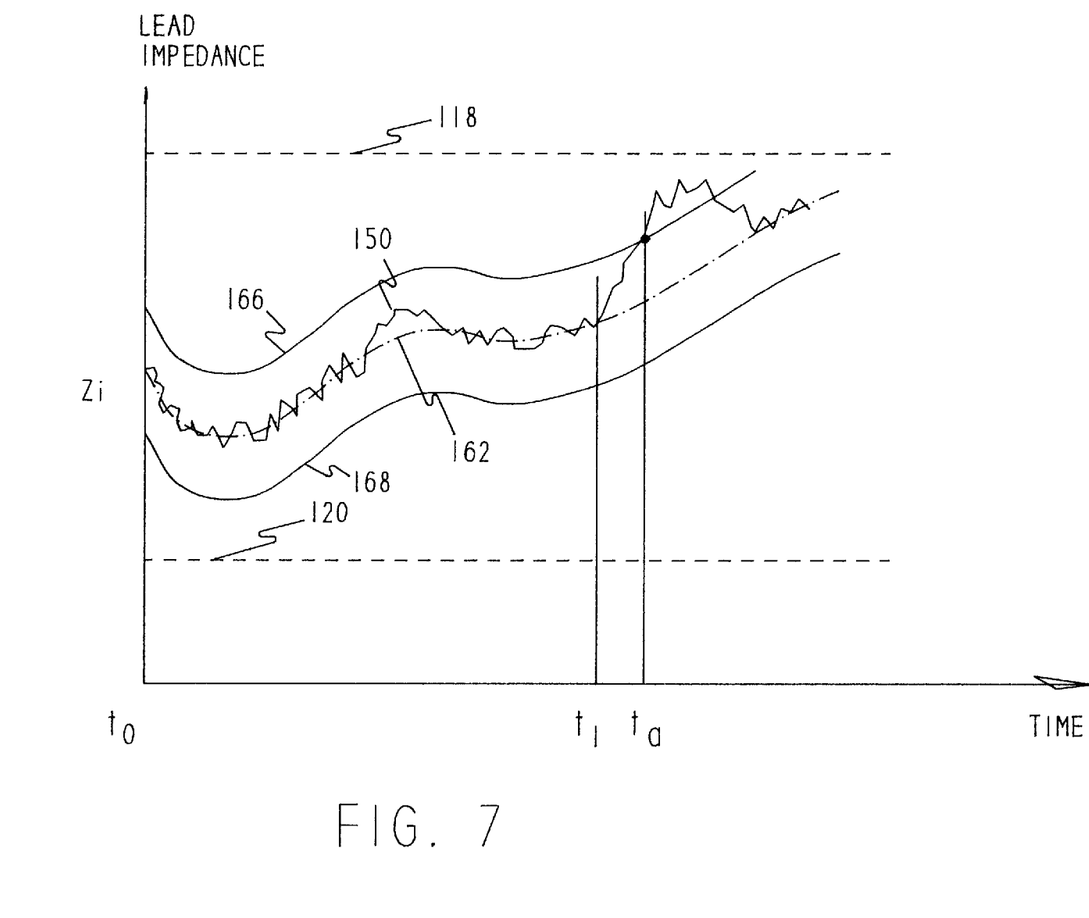
FIG. 7 illustrates a graph showing measured lead impedance as a function of time, along with a moving average of lead impedance, upper and lower dynamic limits of impedance, and maximum and minimum absolute limits of impedance.

Although the absolute maximum limit 118 and the absolute minimum limit 120 may be sufficient to provide an adequate warning of lead failure or impending lead failure, dynamic limits may be used alone or in combination with the absolute limits discussed previously to detect impedance variations that are indicative of lead failure or impending lead failure. The use of dynamic limits is illustrated in FIG. 7 in conjunction with the use of absolute limits, as previously discussed in reference to FIG. 5. It will become apparent during the discussion of FIG. 7 of how the dynamic limits could operate in the absence of the absolute limits 118 and 120.

The curve 150 illustrates the measured impedance of the lead 19 over time. Unlike the curve 100 of FIG. 5 which crossed the absolute maximum limit 118 and, thus, initiated an alarm condition, the impedance curve 150 does not cross either the absolute maximum limit 118 or the absolute minimum limit 120. However, the impedance curve 150 experiences a relatively sharp rise in impedance between time $t_1$ and time $t_a$. This sharp rise in impedance may indicate a lead failure or an impending lead failure. However, because the impedance does not rise above the absolute maximum limit 118, this lead failure or impending lead failure would go unnoticed using the scheme described previously in reference to FIGS. 5 and 6.

Figure 8:
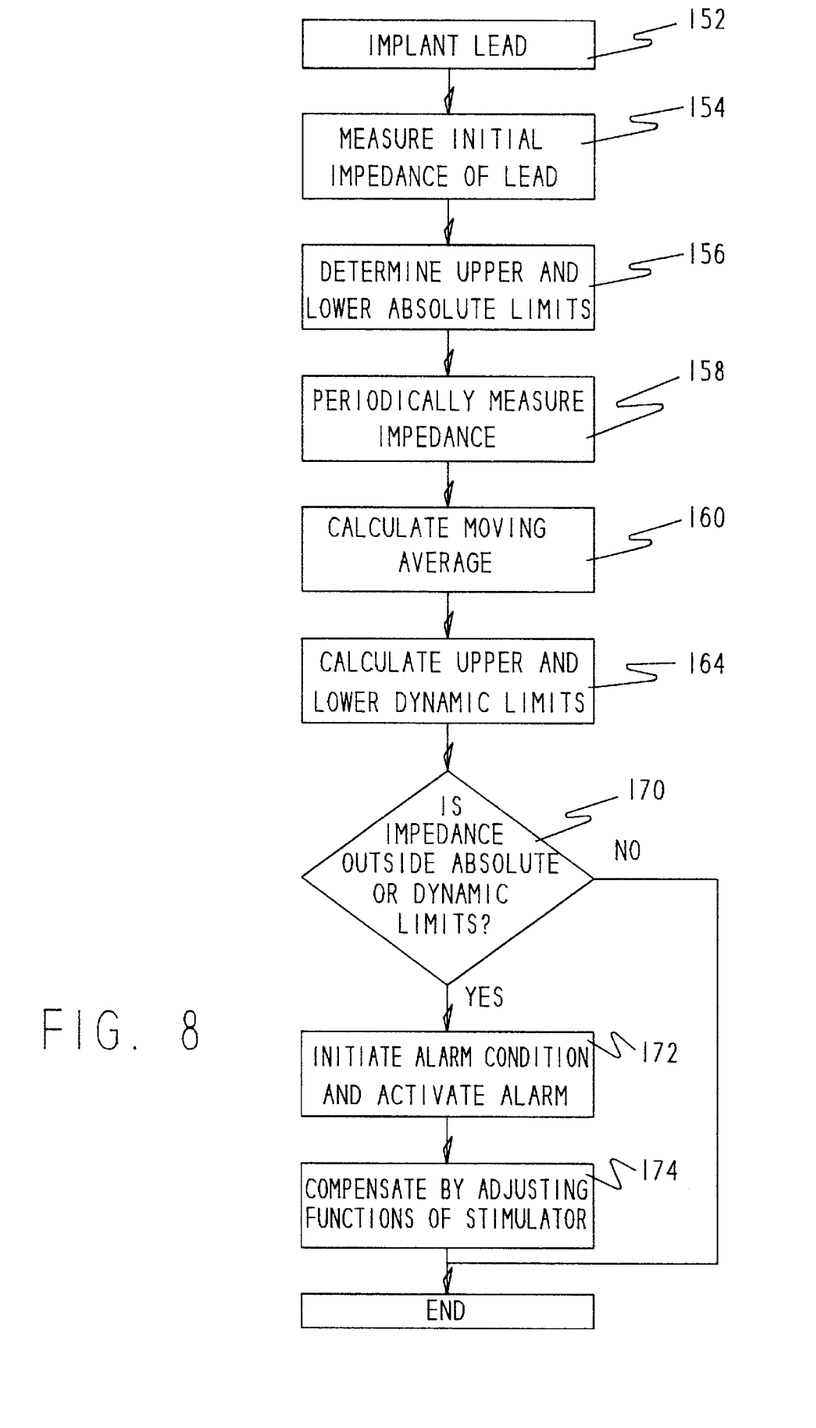
FIG. 8 illustrates a flow chart depicting a failure detection operating mode of the cardiac stimulation system of FIG. 2.

As may be seen by a discussion of FIGS. 7 and 8, the use of dynamic limits permits detection of lead failure or impending lead failure indicated by the sharp rise in impedance between the time $t_1$, and the time $t_a$. At the time $t_0$, the lead 19 is implanted and the initial impedance $Z_i$ of the lead 19 is measured. See blocks 152 and 154. The absolute maximum limit 118 and the absolute minimum limit 120 may be determined in the same manner as set forth above in reference to FIGS. 5 and 6. See block 156. After the initial impedance measurement, the impedance of the lead 19 is periodically measured. See block 158. Each time the impedance of the lead 19 is measured, the microprocessor 28 calculates a moving average of the measured impedance. See block 160. The moving average is illustrated in FIG. 8 as a curve 162. Based on the moving average 162, the microprocessor 28 calculates upper and lower dynamic limits. See block 164. The upper and lower dynamic limits are illustrated in FIG. 7 as curves 166 and 168, respectively. The upper and lower dynamic limits 166 and 168 may be calculated using preset or programmable coefficients. As can be seen from viewing FIG. 7 at time $t_0$, the upper and lower dynamic limits 166 and 168 are smaller in magnitude than the absolute limits 118 and 120.

Once the upper and lower dynamic limits 166 and 168 have been calculated, the measured impedance is compared to the absolute limits 118 and 120 and to the dynamic limits 166 and 168. See block 170. If the measured impedance falls within both the absolute limits 118 and 120 and the dynamic limits 166 and 168, no action is taken. However, if the measured impedance falls outside of the absolute limits 118 or 120 or outside of the dynamic limits 166 or 168 (at time $t_a$, for instance), an alarm condition is initiated and the alarm is activated. See block 172. Additionally, the functionality of the cardiac stimulator 10 may be adjusted to compensate for the alarm condition, as discussed previously. See block 174.

Because leads typically fail due to breakage—a failure mode exemplified by sharp increases in impedance—the embodiments discussed above may be used without the minimum absolute limit 120 and/or the lower dynamic limit 168. Similarly, if detection of a failure mode exemplified by a sharp decrease in impedance, which may be caused by electrode dislocation for instance, is of primary importance in a certain circumstance, the embodiments discussed above may be used without the maximum absolute limit 118 and/or the upper dynamic limit 166.

In addition to the embodiments discussed above, the occasion may exist where warning a patient may be undesirable. In such a situation, the cardiac stimulator 10 may be programmed with one or more of the absolute limits 118 and 120 or dynamic limits 166 and 168. However, instead of triggering a warning signal in response to an impedance measurement being outside one of these limits, the microprocessor 28 may be programmed to alert the patient's physician via the telemetry circuit 42 during a routine check up. In fact, the cardiac stimulator 10 may use a second set of absolute limits and/or dynamic limits having magnitudes smaller than the absolute limits 118 and 120 and the dynamic limits 166 and 168. This second set of limits may be used in conjunction with the absolute limits 118 and 120 and the dynamic limits 166 and 168. In this embodiment, the cardiac stimulator 10 may alert the patient's physician of an impending failure during a routine check up without alarming the patient if the measured impedance falls outside of one of the second set of limits but within the first set of limits. However, if the patient does not visit the physician at an opportune time, or if the failure is severe enough (i.e., the impedance falls outside of one of the first set of limits), the cardiac stimulator 10 may alert the patient by providing warning as discussed above.

While the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A lead failure detector for use with a cardiac stimulator comprising:

means for measuring impedance of a lead;

means for calculating an upper impedance limit and a lower impedance limit;

means for comparing said measured impedance with the upper impedance limit and the lower impedance limit; and means for activating an alarm in response to said measured impedance being one of greater than said upper impedance limit and less than said lower impedance limit.

2. The lead failure detector, as set forth in claim 1, wherein said measuring means comprises:

a resistor coupled in series with a capacitor used for delivering an electrical charge to said lead.

3. The lead failure detector, as set forth in claim 2, wherein said measuring means further comprises:

a first sample and hold circuit coupled to measure voltage across said capacitor; and a second sample and hold circuit coupled to measure current flowing through said resistor.

4. The lead failure detector, as set forth in claim 3, wherein said measuring means further comprises:

a signal processor coupled to receive said measured voltage and said measured current, wherein said signal processor calculates said impedance of said lead based on said measured voltage and said measured current.

5. The lead failure detector, as set forth in claim 1, wherein said comparing means comprises:

a signal processor storing said upper impedance limit and said lower impedance limit, said signal processor comparing said measured impedance with said upper impedance limit and said lower impedance limit, said signal processor delivering an activation signal in response to said measured impedance being one of greater than said upper impedance limit and less than said lower impedance limit.

6. The lead failure detector, as set forth in claim 1, wherein said activating means comprises:

a stimulus generator receiving an activation signal in response to said measured impedance being one of greater than said upper impedance limit and less than said lower impedance limit, said stimulus generator delivering an electrical stimulation charge in response to said activation signal; and an electrode coupled to said stimulus generator to receive said electrical stimulation charge, said electrode being adapted to be coupled to bodily tissue.

7. A lead failure detector for use with a cardiac stimulator comprising:

means for receiving data correlative to repeated impedance measurements of a lead;

means for calculating a maximum impedance limit and a minimum impedance limit in response to a first of said repeated impedance measurements;

means for calculating an upper impedance limit and a lower impedance limit in response to each of said repeated impedance measurements;

means for determining whether said data correlative to each of said repeated impedance measurements is greater than one of said maximum impedance limit and said upper impedance limit and is less than one of said minimum impedance limit and said lower impedance limit; and means for generating an alarm initiation signal in response to said data correlative to one of said repeated impedance measurements being greater than one of said maximum impedance limit and said upper impedance limit or being less than one of said minimum impedance limit and said lower impedance limit.

8. The lead failure detector, as set forth in claim 7, wherein said maximum impedance limit is greater than said upper impedance limit calculated in response to said first of said repeated impedance measurements, and wherein said minimum impedance limit is less than said lower impedance limit calculated in response to said first of said repeated impedance measurements.

9. The lead failure detector, as set forth in claim 7, further comprising:

means for calculating a secondary maximum impedance limit and a secondary minimum impedance limit in response to said first of said repeated impedance measurements, said secondary maximum impedance limit being less than said maximum impedance limit, and said secondary minimum impedance limit being greater than said minimum impedance limit; and means for generating a physician warning signal in response to said data correlative to one of said repeated impedance measurements being greater than said secondary maximum impedance limit and less than said maximum impedance limit or being less than said secondary minimum impedance limit and greater than said minimum impedance limit.

10. The lead failure detector, as set forth in claim 7, further comprising:

means for calculating a secondary upper impedance limit and a secondary lower impedance limit in response to each of said repeated impedance measurements, said secondary upper impedance limit being less than said upper impedance limit, and said secondary lower impedance limit being greater than said lower impedance limit; and means for generating a physician warning signal in response to said data correlative to one of said repeated impedance measurements being greater than said secondary upper impedance limit and less than said upper impedance limit or being less than said secondary lower impedance limit and greater than said lower impedance limit.

11. A lead failure detector for use with a cardiac stimulator comprising:

a lead adapted to transmit electrical signals to a heart of a patient;

means for measuring impedance of said lead;

means for determining whether said measured impedance is within a given impedance range and for delivering an alarm initiation signal in response to said measured impedance being outside said given range; and means for alerting the patient in response to said alarm initiation signal.

12. The lead failure detector, as set forth in claim 11, wherein said measuring means comprises:

a resistor coupled in series with a capacitor used for delivering an electrical charge to said lead.

13. The lead failure detector, as set forth in claim 12, wherein said measuring means further comprises:

a first sample and hold circuit coupled to measure voltage across said capacitor; and a second sample and hold circuit coupled to measure current flowing through said resistor.

14. The lead failure detector, as set forth in claim 13, wherein said measuring means further comprises:

a signal processor coupled to receive said measured voltage and said measured current, wherein said signal processor calculates said impedance of said lead based on said measured voltage and said measured current.

15. The lead failure detector, as set forth in claim 11, wherein said determining means comprises:

a signal processor storing at least an upper impedance limit, said signal processor comparing said measured impedance with said upper impedance limit, said signal processor delivering said alarm initiation signal in response to said measured impedance being greater than said upper impedance limit.

16. The lead failure detector, as set forth in claim 11, wherein said alerting means comprises:

a stimulus generator receiving said alarm initiation signal, said stimulus generator delivering an electrical stimulation charge in response to said alarm initiation signal; and an electrode coupled to said stimulus generator to receive said electrical stimulation charge, said electrode being adapted to be coupled to bodily tissue.

17. A lead failure detector for use with a cardiac stimulator comprising:

a lead adapted to transmit electrical signals;

an impedance measurement circuit for measuring impedance of said lead;

a comparison circuit for comparing said measured impedance with an impedance limit, said comparison circuit delivering an alarm initiation signal in response to said measured impedance differing from said impedance limit by a given magnitude; and an alarm circuit for alerting a patient in response to said alarm initiation signal.

18. The lead failure detector, as set forth in claim 17, wherein said impedance measurement circuit comprises:

a resistor coupled in series with a capacitor used for delivering an electrical charge to said lead.

19. The lead failure detector, as set forth in claim 18, wherein said impedance measurement circuit further comprises:

a first sample and hold circuit coupled to measure voltage across said capacitor; and a second sample and hold circuit coupled to measure current flowing through said resistor.

20. The lead failure detector, as set forth in claim 19, wherein said impedance measurement circuit further comprises:

a signal processor coupled to receive said measured voltage and said measured current, wherein said signal processor calculates said impedance of said lead based on said measured voltage and said measured current.

21. The lead failure detector, as set forth in claim 17, wherein said comparison circuit comprises:

a signal processor storing said impedance limit, said signal processor comparing said measured impedance with said impedance limit, said signal processor delivering said alarm initiation signal in response to said measured impedance being greater than said impedance limit if said impedance limit represents a maximum impedance, and said signal processor delivering said alarm initiation signal in response to said measured impedance with less than said impedance limit if said impedance limit represents a minimum impedance.

22. The lead failure detector, as set forth in claim 17, wherein said alarm circuit comprises:

a stimulus generator receiving said alarm initiation signal, said stimulus generator delivering an electrical stimulation charge in response to said alarm initiation signal; and an electrode coupled to said stimulus generator to receive said electrical stimulation charge, said electrode being adapted to be coupled to bodily tissue.

23. A lead failure detector for use with a cardiac stimulator, comprising:

a lead adapted to transmit electrical signals to a heart;

an impedance measurement circuit coupled to said lead;

a control circuit coupled to said impedance measurement circuit, said impedance measurement circuit measuring impedance of said lead in response to receiving a first control signal from said control circuit;

a comparison circuit determining whether said measured impedance is within a first impedance range and a second impedance range, said comparison circuit delivering an alarm initiation signal in response to said measured impedance being outside at least one of the first impedance range and the second impedance range; and an alarm circuit delivering an alarm in response to said alarm initiation signal.

24. The lead failure detector, as set forth in claim 23, wherein said impedance measurement circuit comprises:

a resistor coupled in series with a capacitor used for delivering an electrical charge to said lead.

25. The lead failure detector, as set forth in claim 24, wherein said impedance measurement circuit further comprises:

a first sample and hold circuit coupled to measure voltage across said capacitor; and a second sample and hold circuit coupled to measure current flowing through said resistor.

26. The lead failure detector, as set forth in claim 25, wherein said impedance measurement circuit further comprises:

a signal processor coupled to receive said measured voltage and said measured current, wherein said signal processor calculates said impedance of said lead based on said measured voltage and said measured current.

27. The lead failure detector, as set forth in claim 23, wherein said comparison circuit comprises:

a signal processor storing the first impedance range and the second impedance range, the signal processor comparing the measured impedance with the first impedance range and the second impedance range, the signal processor delivering the alarm initiation signal in response to the measured impedance being outside at least one of the first impedance range and the second impedance range.

28. The lead failure detector, as set forth in claim 23, wherein said alarm circuit comprises:

a stimulus generator receiving said alarm initiation signal, said stimulus generator delivering an electrical stimulation charge in response to said alarm initiation signal; and an electrode coupled to said stimulus generator to receive said electrical stimulation charge, said electrode being adapted to be coupled to bodily tissue.

29. A computer-readable medium containing a software program for use with a cardiac stimulator, said program comprising:

a routine for receiving data correlative to an impedance measurement of a lead;

a routine for determining whether said impedance measurement data is within a first impedance range and a second impedance range; and a routine for generating an alarm initiation signal in response to said measured impedance being outside at least one of the first impedance range and the second impedance range.

30. The computer-readable medium, as set forth in claim 29, wherein said receiving routine comprises:

a routine for receiving data correlative to voltage across said lead and data correlative to current through said lead and for calculating an impedance of said lead based on said data correlative to voltage across said lead and said data correlative to current through said lead.

31. The computer-readable medium, as set forth in claim 30, wherein said determining routine comprises:

a routine for comparing said impedance of said lead with an impedance limit.

32. The computer-readable medium, as set forth in claim 31, wherein said generating routine comprises:

a routine for delivering said alarm initiation signal in response to said measured impedance being greater than said impedance limit if said impedance limit represents a maximum impedance and for delivering said alarm initiation signal in response to said measured impedance being less than said impedance limit if said impedance limit represents a minimum impedance.

33. A computer-readable medium containing a software program for use with a cardiac stimulator, said program comprising:

a routine for receiving data correlative to repeated impedance measurements of a lead;

a routine for calculating a maximum impedance limit and a minimum impedance limit in response to a first of said repeated impedance measurements;

a routine for calculating an upper impedance limit and a lower impedance limit in response to each of said repeated impedance measurements;

a routine for determining whether said data correlative to each of said repeated impedance measurements is greater than one of said maximum impedance limit and said upper impedance limit and is less than one of said minimum impedance limit and said lower impedance limit; and a routine for generating an alarm initiation signal in response to said data correlative to one of said repeated impedance measurements being greater than one of said maximum impedance limit and said upper impedance limit or being less than one of said minimum impedance limit and said lower impedance limit.

34. A method of detecting failure of a lead used with a cardiac stimulator, said method comprising the steps of:

(a) measuring impedance of a lead;

(b) comparing said impedance of said lead with an impedance limit; and (c) alerting a patient in response to said impedance of said lead differing from said impedance limit in a given manner.

35. The method, as set forth in claim 34, wherein step (a) comprises the steps of:

measuring a voltage correlative to a voltage across said lead;

measuring a current correlative to a current flowing through said lead; and calculating an impedance of said lead based on said measured voltage and said measured current.

36. The method, as set forth in claim 34, wherein step (b) comprises the steps of:

delivering an alarm initiation signal in response to said impedance being greater than said impedance limit if said impedance limit represents a maximum impedance; and delivering said alarm initiation signal in response to said impedance being less than said impedance limit if said impedance limit represents a minimum impedance.

37. The method, as set forth in claim 36, wherein step (c) comprises the step of:

activating said alarm in response to receiving said alarm initiation signal.

38. A method of detecting failure of a lead used with a cardiac stimulator, said method comprising the steps of:

(a) repeatedly measuring impedance of said lead;

(b) calculating a moving impedance average correlative to the repeated impedance measurements;

(c) calculating an impedance range correlative to the moving impedance average;

(d) determining whether said impedance of said lead is within the calculated impedance range; and (e) generating an alarm initiation signal in response to said impedance of said lead being outside the calculated impedance range.

39. The method, as set forth in claim 38, wherein step (a) comprises the steps of:

measuring a voltage correlative to a voltage across said lead;

measuring a current correlative to a current flowing through said lead; and calculating an impedance of said lead based on said measured voltage and said measured current.

40. The method, as set forth in claim 38, wherein step (d) comprises the steps of:

comparing said impedance to a maximum impedance limit; and comparing said impedance to a minimum impedance limit.

41. The method, as set forth in claim 40, wherein step (e) comprises the steps of:

delivering said alarm initiation signal in response to said impedance being greater than said maximum impedance limit; and delivering said alarm initiation signal in response to said impedance being less than said minimum impedance limit.

42. A method of detecting failure of a lead used with a cardiac stimulator, said method comprising the steps of:

(a) repeatedly measuring impedance of said lead;

(b) calculating a maximum impedance limit and a minimum impedance limit in response to a first of said repeated impedance measurements;

(c) calculating an upper impedance limit and a lower impedance limit in response to each of said repeated impedance measurements;

(d) determining whether each of said repeated impedance measurements is greater than one of said maximum impedance limit and said upper impedance limit and is less than one of said minimum impedance limit and said lower impedance limit; and (e) generating an alarm initiation signal in response to one of said repeated impedance measurements being greater than one of said maximum impedance limit and said upper impedance limit or being less than one of said minimum impedance limit and said lower impedance limit.

* * * * *